United States Patent
Trout et al.

(10) Patent No.: US 10,762,980 B2
(45) Date of Patent: Sep. 1, 2020

(54) COMPUTER-IMPLEMENTED METHODS OF DETERMINING PROTEIN VISCOSITY

(71) Applicants: Massachusetts Institute of Technology, Cambridge, MA (US); Novartis Pharma AG, Basel (CH)

(72) Inventors: Bernhardt Levy Trout, Lexington, MA (US); Bernhard Helk, Loerrach (DE); Neeraj Jagdish Agrawal, Thousand Oaks, CA (US)

(73) Assignees: Massachusetts Institute of Technology, Cambridge, MA (US); Novartis Pharma AG, Basel (CH)

( * ) Notice: Subject to any disclaimer, the term of this patent is extended or adjusted under 35 U.S.C. 154(b) by 0 days.

(21) Appl. No.: 14/891,906

(22) PCT Filed: May 16, 2014

(86) PCT No.: PCT/US2014/038368
§ 371 (c)(1),
(2) Date: Nov. 17, 2015

(87) PCT Pub. No.: WO2014/186692
PCT Pub. Date: Nov. 20, 2014

(65) Prior Publication Data
US 2016/0132634 A1    May 12, 2016

Related U.S. Application Data

(60) Provisional application No. 61/824,680, filed on May 17, 2013.

(51) Int. Cl.
G16B 15/00 (2019.01)
G01N 33/68 (2006.01)
G01N 11/00 (2006.01)

(52) U.S. Cl.
CPC ............ *G16B 15/00* (2019.02); *G01N 11/00* (2013.01); *G01N 33/6803* (2013.01); *G01N 33/6854* (2013.01); *G01N 2011/006* (2013.01)

(58) Field of Classification Search
None
See application file for complete search history.

(56) References Cited

PUBLICATIONS

Allison et al. Macromolecules 1998, 31, 4464-4474.*
Zhou et al. Biophysical Journal, 1995, 69, pp. 2298-2303.*
Reed et al. Drug Development Research, 2004, 61:137-154.*
Aragon et al., The intrinsic viscosity of proteins from high precision boundary element calculations. Biophysical J. Jan. 2004;86(1):624a. 48th Annual Meeting of the Biophysical Society. Abstract.
Chaudhri et al., Coarse-grained modeling of the self-association of therapeutic monoclonal antibodies. J Phys Chem B. Jul. 19, 2012;116(28):8045-57. doi: 10.1021/jp301140u. Epub Jul. 6, 2012.
Harding, The intrinsic viscosity of biological macromolecules. Progress in measurement, interpretation and application to structure in dilute solution. Prog Biophys Mol Biol. 1997;68(2-3):207-62.
Ketchem et al., Mitigation of monoclonal antibody viscosity by modification of protein surface charge. American Chemical Society. Abstracts of Papers. Mar. 2012;243:1. Abstract.
Yadav et al., The influence of charge distribution on self-association and viscosity behavior of monoclonal antibody solutions. Mol Pharm. Apr. 2, 2012;9(4):791-802. doi: 10.1021/mp200566k. Epub Mar. 19, 2012.
Bethea et al., Mechanisms of self-association of a human monoclonal antibody CNT0607. Protein Eng Des Sel. Oct. 2012;25(10):531-7. Epub Aug. 22, 2012.
Roskos et al., The clinical pharmacology of therapeutic monoclonal antibodies. Drug Dev Res. Mar. 2004;61(3):108-120.
Shire et al., Challenges in the development of high protein concentration formulations. J Pharm Sci. Jun. 2004;93(6):1390-402.
Teplyakov etal., Epitope mapping of anti-interleukin-13 neutralizing antibody CNTO607. J Mol Biol. May 29, 2009;389(1):115-23. doi: 10.1016/j.jmb.2009.03.076. Epub Apr. 8, 2009.
Yadav et al., Viscosity analysis of high concentration bovine serum albumin aqueous solutions. Pharm Res. Aug. 2011;28(8):1973-83. doi:10.1007/s11095-011-0424-7. Epub Apr. 14, 2011.
Yadav et al., Viscosity behavior of high-concentration monoclonal antibody solutions: correlation with interaction parameter and electroviscous effects. J Pharm Sci. Mar. 2012;101(3):998-1011. doi:10.1002/jps.22831. Epub Nov. 23, 2011.

* cited by examiner

*Primary Examiner* — Michael L Borin
(74) *Attorney, Agent, or Firm* — Wolf, Greenfield & Sacks, P.C.

(57) ABSTRACT

Provided herein are high-throughput methods for identifying a candidate antibody based on viscosity of the candiate antibody.

12 Claims, 8 Drawing Sheets

(entire central region is red to various degrees)

COMPUTER-IMPLEMENTED METHODS OF DETERMINING PROTEIN VISCOSITY

RELATED APPLICATIONS

This application is a national stage filing under 35 U.S.C. § 371 of International Application No. PCT/US2014/038368, filed May 16, 2014, which was published under PCT Article 21(2) in English, and which claims the benefit under 35 U.S.C. § 119(e) of U.S. Provisional Application Ser. No. 61/824,680, filed on May 17, 2013, the entire contents of each of which are incorporated herein by reference.

FIELD OF THE INVENTION

Aspects of the invention relate to computer-implemented methods for predicting viscosities of compositions comprising proteins (such as antibodies) and screening proteins based on the predicted viscosities.

BACKGROUND OF INVENTION

Many therapeutic proteins such as, for example, antibodies may be administered via subcutaneous injection. This injection pathway requires a high protein concentration in the final solution to be injected (Shire et al., *J Pharm Science*, 2004; 93(6): 1390-1402; Roskos et al., *Drug Devel Res*, 2004; 61(3): 108-120). Achieving the high protein concentration necessary for subcutaneous delivery can be problematic.

SUMMARY OF INVENTION

Some embodiments of techniques described herein provide computer-implemented methods for automatically and quantitatively predicting the viscosity of a solution comprising a protein based on information regarding the protein, such as information regarding the structure or other properties of the protein. Information regarding the protein may be input, for example, in the form of a computer-generated structure of the protein, such as a predicted structure of the protein following folding. Analysis of that computer-generated structure or information regarding the computer-generated structure may be quantitatively analyzed using the techniques described herein to identify anticipated structural properties of the protein and, based on those properties, form a prediction of the viscosity of a particular solution comprising that protein. In some embodiments, techniques are also provided for screening proteins (such as, but not limited to, antibodies) based on their viscosities in solution, providing a convenient, rapid and inexpensive way to identify those proteins more likely to be of interest as candidates. As used herein, a candidate is a protein (such as an antibody) typically selected from a plurality of proteins based on a particular characteristic (e.g., viscosity) and that may be used and/or further developed. Candidates include clinical candidates, intending candidates that will be used and/or further developed for use in vivo.

Viscosity of antibodies has been previously studied, but the inventors have recognized and appreciated limitations of this prior work. The prior approaches were limited to determining an electrostatic potential of a protein's surface and identifying, based on that potential, whether the studied antibodies would be highly viscous. Visual inspection of individual antibodies by a human user was a necessary part of that analysis. The inventors recognized and appreciated that this approach was cumbersome and slow to use, at least due to the required visual inspection of each antibody. Worse, the inventors recognized and appreciated that the evaluation of electrostatic potential was qualitative and that the electrostatic potential scales used in this previous work limited the accuracy of the approach to no-better-than average.

In contrast, the computer-implemented methods provided herein are quantitative. As laid out below, whereas the prior techniques exclusively relied on human assessments of an antibody's electrostatic potential to determine viscosity, a viscosity prediction facility as described herein, executing on one or more computing devices, may analyze computer-generated information on a predicted structure of a protein (e.g., a structure following folding of the protein) to identify several anticipated structural properties of that protein. The viscosity prediction facility may then, in accordance with some of the techniques described herein, evaluate those anticipated structural properties and perform calculations on numeric values regarding those anticipated properties to produce a numeric value. Such calculations may, in some embodiments, additionally be performed using information regarding a desired solution including the protein. The numeric value produced using techniques described herein correlates with viscosity of the protein, or of the solution including the protein, that was analyzed. In some embodiments, therefore, the viscosity prediction facility may additionally evaluate the numeric value to form a prediction of the viscosity of that protein/solution.

Accordingly, described herein are computer-implemented techniques that, for each protein, (i) perform calculations based on evaluations of numeric values indicative of anticipated properties of the protein and (ii) report a numeric result that can be used to classify a protein as potentially having low or high viscosity. The computer-implemented techniques do not require visual inspection or qualitative analysis by a human user and, since the techniques described herein do not use the electrostatic scale used in the prior visualization techniques, the accuracy can be improved beyond that previously offered. Furthermore, as the approaches are completely quantitative, they facilitate high-throughput analysis. Lastly, since SCM is quantitative, it is easily extended to multiple structures of the protein obtained using molecular dynamic simulation.

In some embodiments, a viscosity prediction facility may perform an analysis referred to herein as a spatial charge map (SCM). SCM is a computational, predictive, high-throughput analysis that aids in the discovery and development of proteins. In some embodiments, the proteins are antibodies including monoclonal antibodies (mAbs). SCM allows for rapid in silico screening of proteins based on their viscosities. As used herein, viscosity of a protein refers to viscosity of a composition such as a solution comprising such protein. The SCM analysis can be performed during the early stages of a development process and can lead to identification of proteins with desirable viscosity profiles. This knowledge can be used to prioritize protein candidates for further development.

Various aspects and embodiments of the invention are described in terms of antibodies and more specifically monoclonal antibodies. However it is to be understood that the invention embraces proteins generally, and that the recitations relating to antibodies are to be understood as exemplary of the broader class of proteins.

SCM is described in detail below. Briefly, SCM involves as a first step obtaining a three-dimensional or tertiary structure(s) of the protein of interest, such as an antibody.

This may be done experimentally or it may be done in silico by converting the primary amino acid sequence of a protein (or a protein fragment or domain, such as an antibody fragment or antibody domain) to a three dimensional or tertiary structure(s). This may be done, for example, using homology modeling. The structure is then analyzed using SCM. SCM relies, in part, on negative charges or regions of negative charge on the solvent accessible surface of proteins. SCM can be analyzed under one or more conditions or environments such as pH, and a single SCM value will be output for each condition. As an example, a SCM score may be determined for a protein at pH of greater than or equal to 7 and at a pH less than or equal to about 5.5, with one SCM value being output for each pH. The value of SCM Score correlates with the viscosity of the protein (or a solution comprising the protein, as used interchangeably herein).

Thus, in one aspect, the invention provides a method of determining viscosity of a protein, the method comprising, analyzing a representation of a structure of the protein or a portion of the protein to compute a score for the protein (or portion thereof) based on a parameter of each atom in the structure under a condition, and determining viscosity of the protein based on the computed score. In some embodiments, the protein is an antibody such as a monoclonal antibody.

In another aspect, the invention provides a computer-implemented method of determining viscosity of a protein such as an antibody, the method comprising, by at least one processor, analyzing a representation of at least one structure of at least a portion of the protein to compute a score for the at least a portion of the protein based on at least one parameter of each atom in the at least one structure under at least one condition, and determining the viscosity of the protein based on the computed score. In some embodiments, the protein is an antibody such as a monoclonal antibody.

In another aspect, the invention provides a method of identifying one or more candidates from a plurality of proteins. The candidate proteins may be clinical candidates to be used or to be developed further. The method comprises generating at least one molecular structure of at least a portion of an protein from the plurality of proteins, analyzing the least one molecular structure to compute a score for the at least a portion of the protein based on a partial charge and solvent exposure of each atom in the at least one molecular structure under at least one condition, predicting viscosity of the protein based on the computed score, and identifying the protein as a candidate of interest based on the predicted viscosity of the protein. In some embodiments, the protein is an antibody such as a monoclonal antibody.

In yet another aspect, the invention provides a method of screening a plurality of proteins to identify candidates for use or development, the method comprising computing a score for at least a portion of a protein from the plurality of proteins based on partial charges and solvent exposures of atoms in at least one molecular structure of the at least a portion of a protein, wherein the computed score is correlated with viscosity of the protein; and selecting the protein as a protein candidate based on the computed score. In some embodiments, the protein is an antibody such as a monoclonal antibody.

These and other aspects and embodiments of the invention will be described in greater detail herein.

BRIEF DESCRIPTION OF FIGURES

FIG. 5A is a color rendering.

DETAILED DESCRIPTION OF INVENTION

Figure 1:
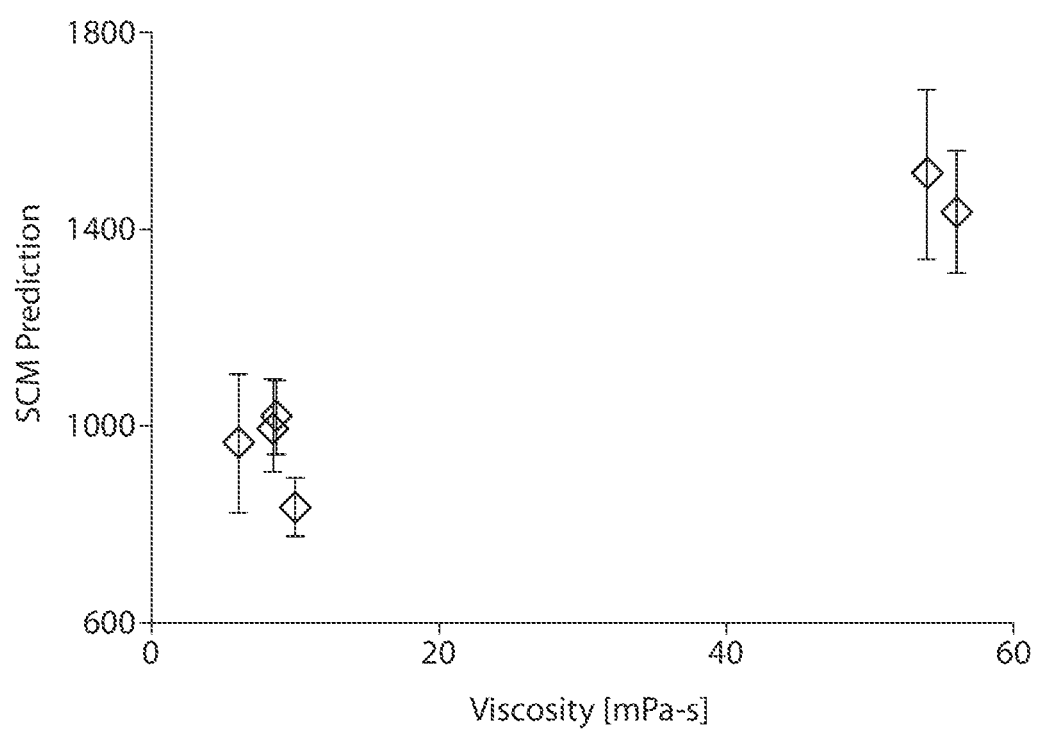
FIG. 1 is a plot of SCM prediction versus experimentally obtained viscosity. The x-axis is the experimentally measured viscosity of six different IgG1 mAbs (mAb concentration=150 mg/ml, 20 mM Histidine, 220 mM Sucrose, 0.04% PS-20, pH 5.5).

Compositions containing proteins (e.g., monoclonal antibodies) are, in many instances, injected or infused via subcutaneous injection. Subcutaneous injection, in many instances, conveniently can be performed outside of a clinical setting and without a medical practitioner's assistance. However, viscoelastic resistance to hydraulic conductance in the subcutaneous tissue, backpressure generated upon injection, and perceptions of pain all limit subcutaneous injection volumes to small volumes sometimes on the order of approximately 2 ml. Therefore, protein compositions intended for subcutaneous injection usually are highly concentrated and thus also highly viscous. It is this latter property that further limits their utility.

Described herein are computer-based utilities, referred to as viscosity prediction facilities, for analyzing computer-generated information regarding a protein of interest (e.g., an antibody), inferring anticipated structural properties of the protein, and performing computations on information regarding the anticipated structural properties. The computations described herein and performed by the facilities may yield numeric values that correlate with viscosity. Such computations may, in some cases, be additionally performed using information on a desired solution including the protein, to yield information on predicted viscosity in the desired solution. The facilities may also analyze the numeric value output from the computations to make a prediction of a viscosity of the protein/solution.

A viscosity prediction facility may be implemented using any of various techniques described herein. Spatial charge map (SCM) is one technique described herein for analyzing a computer-generated information regarding an anticipated structure of a protein to yield information on a predicted viscosity. Below, a viscosity prediction facility implementing SCM is referred to as an SCM tool. Viscosity prediction facilities (including SCM tools) described herein may execute on one or more computing devices to evaluate information regarding protein(s) and/or solution(s) and identify candidates based on predictions regarding viscosities.

For convenience, viscosity prediction techniques are described below in terms of analyzing antibodies, but it is to be understood that these techniques may be applied to other proteins as well. The proteins may be clinical candidates although they are not so limited.

An SCM tool may be implemented as a structure-based phenomenological molecular-modeling tool, which identifies patches of charged residues on the protein surface. In embodiments, the input to an SCM tool is a structure of the protein such as an antibody. If the structure is not available experimentally, homology-modeling software can be used to model the structure of the protein using its sequence. It is to be understood that the structure modeling can be done using either an amino acid sequence or a nucleic acid sequence. The following describes various steps that may be carried out by an SCM tool, in the context of antibodies, to form a prediction of viscosity based on computer-generated information regarding the structure of an antibody. The steps may be performed on non-antibody proteins also.

As a first step, the SCM tool assigns each atom in the antibody a partial charge. The SCM tool can obtain the partial charge in a variety of ways, including using software like PropKa or directly borrowed from force fields. In the exemplifications provided herein, partial charges on each protein atom are borrowed using CHARMM27 force field. Since the partial charges on atoms are typically dependent on the formulation conditions including the formulation pH, the SCM calculation is preferably performed at various pH values if the dependence of viscosity on formulation pH is needed.

Based on the protein structure and the atomic partial charges at the formulation pH, the SCM tool computes an SCM value of each atom using the following equation if a single structure of the protein is available:

$$SCM_{atom,i} = \sum_{\substack{\text{side-chain atoms,} \\ \text{which belong to an} \\ \text{exposed residue and} \\ \text{are within distance R} \\ \text{of the atom } i}} \text{partial charge of the atom} \quad (1)$$

In Eq. 1, the SCM tool considers a residue to be an exposed residue if the total solvent accessible area (computed using water with probe radius of 1.4 Å) of all the side-chain atoms of the residue in the protein structure is greater than a particular cut-off. The cut-off may be any cut-off in and between 1 to 50 Å². In some embodiments, the cut-off may be 10 Å². In Eq. 1, the value of distance 'R' is greater than zero. In the various exemplifications provided herein, an SCM tool may compute SCM values at R=5 and 10 Å. In general, an SCM tool may compute an SCM score at any value of R, which is greater than zero. R values ranging from 5-20 Å can be used with the understanding the lower R values provide higher resolution but more noise and conversely the higher R values provide lower resolution but less noise.

In the context of antibodies, once the SCM value for each of the atoms is computed, the SCM tool computes a variety of SCM scores for various domains of the antibody as:

$$Fab\ SCM\ \text{Score} = \sum_{\substack{\text{all atoms in} \\ \text{the Fab domain}}} SCM_{atom,i} \quad (2)$$

$$Fab\ \text{positive}\ SCM\ \text{Score} = \sum_{\substack{\text{all atoms in} \\ \text{the Fab domain}}} SCM_{atom,i} \times H(SCM_{atom,i}) \quad (3)$$

$$Fab\ \text{negative}\ SCM\ \text{Score} = \sum_{\substack{\text{all atoms in} \\ \text{the Fab domain}}} SCM_{atom,i} \times H(-SCM_{atom,i}) \quad (4)$$

$$Fv\ SCM\ \text{Score} = \sum_{\substack{\text{all atoms in} \\ \text{the Fv domain}}} SCM_{atom,i} \quad (5)$$

$$Fv\ \text{positive}\ SCM\ \text{Score} = \sum_{\substack{\text{all atoms in} \\ \text{the Fv domain}}} SCM_{atom,i} \times H(SCM_{atom,i}) \quad (6)$$

$$Fv\ \text{negative}\ SCM\ \text{Score} = \sum_{\substack{\text{all atoms in} \\ \text{the Fv domain}}} SCM_{atom,i} \times H(-SCM_{atom,i}) \quad (7)$$

where $H(x)$ is the Heaviside function (i.e., $H(x)=1$ for $x \geq 0$, $H(x)=0$ for $x<0$). The SCM tool can similarly compute corresponding SCM scores of the CDR.

If multiple structures or conformations of the antibody are available, an SCM tool may compute the averages and the standard deviations of the above-mentioned SCM scores (Eqns. 2-7) after computing the atomic SCM values and the SCM scores for each structure or conformation of the antibody.

The steps an SCM tool, executing on one or more computing devices, may take to compute the SCM score of an antibody are described below.

Step 1. Structure of the Fab Domain:

Obtain the structure of the Fab domain of the antibody. If the structure of the Fab domain is not available from experiments, the structure can be modeled using a variety of available software like WAM, PEGS, Rosetta, Accelrys, MOE, Schrodinger, etc. Some of these software packages generate coordinates for heavy atoms and hydrogen atoms of a protein. Examples include Accelrys, MOE and Schrodinger. Others generate coordinates for only heavy atoms. Examples include WAM, PEGS and Rosetta. If the latter class of package is used, a subsequent step is performed to generate the coordinates of the hydrogen atoms.

Step 2. Partial Charge of Each Atom at the Formulation pH:

A variety of available software packages like PropKa, Accelrys, Schrodinger, etc. can be used to deduce the partial charge on each atom of the Fab domain at the formulation pH. In the simulations provided herein, partial charges are assigned to the atoms using the CHARMM27 force field. At a pH>pKa of Histidine, it is assumed that all Histidine residues have neutral side chains while at a pH<pKa of Histidine, it is assumed that all Histidine residues have positively charged side chains. The pKa of Histidine is about 6.2-6.5. Other methods of assigning protonation states to Histidine side chain can also be employed.

Step 3. Compute SAA of Each Residue in the Protein:

For each residue, the total solvent accessible area (SAA) of all its side-chain atoms is computed using the structure of the protein.

Step 4: Identify Exposed Residues:

All residues with SAA>10 Å$^2$ are classified as exposed residues (i.e., surface exposed residues) and residues with SAA<10 Å$^2$ are classified as buried residues. A different threshold for this area cutoff can also be used.

Step 5. Compute Atomic SCM Values:

For every atom 'i' in the protein, all protein atoms are identified which (1) are within distance R of this atom 'i' and (2) belong to the side-chain of an exposed residue. The atomic SCM value of atom 'i' of the protein is then the sum of partial charges of all these atoms. Any value of R>0 can be used; in the simulations provided herein, R=10 Å is used.

Step 6. SCM Score:

Eqns. 3-7 are used to compute various SCM Scores of the various domains.

Step 7. Multiple Conformations:

If there are multiple structures or conformations of the Fab domain, steps 3-6 are repeated, thereby obtaining the average and the standard deviation of various SCM Scores over these multiple structures or conformations.

Step 8. SCM Projection:

The SCM tool also allows the visualization of the atomic SCM values projected on the protein surface. Each atom of the protein can be colored according to its SCM value. For example, an atom with a SCM value>0 can be colored in blue and an atom with a SCM value<0 can be colored in red.

In one example, the SCM tool may use the absolute value of 'Fv negative SCM Score' computed at R=10 Å as the SCM prediction. For each mAb, the SCM tool may perform a 20 ns molecular dynamics simulation and may extract 100 conformations from the last 10 ns of the simulation at an interval of 100 ps. The SCM tool may also compute average and the standard deviations in the absolute value of 'Fv negative SCM Score.' A high absolute value of the 'Fv negative SCM Score' is correlated with a high viscosity of the mAb.

In some instances, the SCM tool may use a cutoff between low and high viscosity of about 900.

In some instances, the SCM tool may not use a strict cutoff and rather may present (e.g., display) SCM scores for a variety of antibodies to an end user. The end user may select antibodies of interest by comparing SCMs of the variety of antibodies. Thus, viscosity may be considered to be relative viscosity in some instances of the invention.

The SCM tool can identify candidates with high viscosity in a high-throughput fashion early in the discovery phase. This would allow highly viscous mAb candidates to be excluded early in the development phase. In one study, experimentally measured viscosities of six IgG1 mAbs under similar conditions were used to validate the SCM-based method. As shown in FIG. 1, there was good correlation between the viscosity of the mAb and its absolute Fv negative SCM Score.

Figure 2:
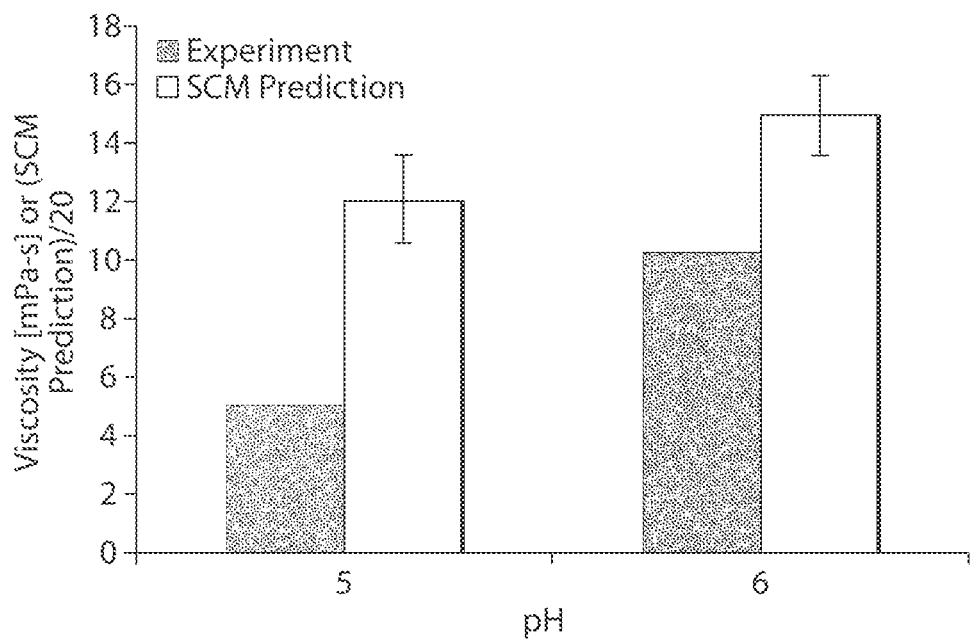
FIG. 2 is a comparison of SCM predictions at two different pH values for mAb10 with experimentally measured viscosity of mAb10. Experiments were performed using 100 mg/ml of mAb10 in 10 mM His buffer in presence of 200 mM Trehalose and 0.03 mM Tween 80. Experimental values are in the first bar of each pair. SCM predicted values are in the second bar of each pair.

In general, there is a lack of available experimental data on viscosities of mAbs measured under similar conditions. Since viscosity of mAb is highly dependent on mAb concentration, formulation conditions (e.g., excipients, buffer, pH, etc.), and the like, the available experimental data for different mAbs measured under dissimilar conditions cannot be compared quantitatively to the SCM predictions. In FIG. 2, a qualitative validation is performed of the SCM predictions against the experimental data measured under dissimilar conditions.

Table 1 provides results of a qualitative validation of the SCM predictions against the viscosities measured under dissimilar conditions (e.g., different formulations, excipients, pH ~5.5, mAb concentration>100 mg/ml) for various IgG1 mAbs. SCM predictions are made at pH ~5.5. Viscosity of CNTO607 is reported in ref. 4 and the structure of CNTO607 is reported in ref. 5. mAb1, mAb2, mAb4, and Rituximab have viscosity lower than 10 mPa-s while mAb5-mAb8, and CNTO607 have viscosity higher than 10 mPa-s. Excipients like Glycine and Arginine lead to viscosity reduction of antibody formulations. As shown in Table 1, a high value of the absolute Fv negative SCM Score is a good indicator of the high viscosity of the mAb.

TABLE 1

A qualitative validation of the SCM predictions against the viscosities measured under dissimilar conditions

| IgG1 mAb | SCM Prediction | Experimental Viscosity [mPa-s] | Notes |
|---|---|---|---|
| mAb1 | 1002 ± 95 | 8.5 | |
| mAb2 | 1020 ± 76 | 8.7 | |
| mAb4 | 965 ± 142 | 6.1 | |
| Rituxan | 836 ± 59 | 10 | |
| mAb5 | 1183 ± 135 | 20 | 60 mM Glycine |
| mAb6 | 1513 ± 174 | 22 | |
| mAb7 | 1476 ± 177 | 11 | 51 mM Arginine |
| mAb8 | 1291 ± 117 | >50 | |
| CNTO607 | 1773 ± 73 | High | |

The SCM-based method can rank the viscosity of different mAbs as a function of formulation pH.

Figure 3:
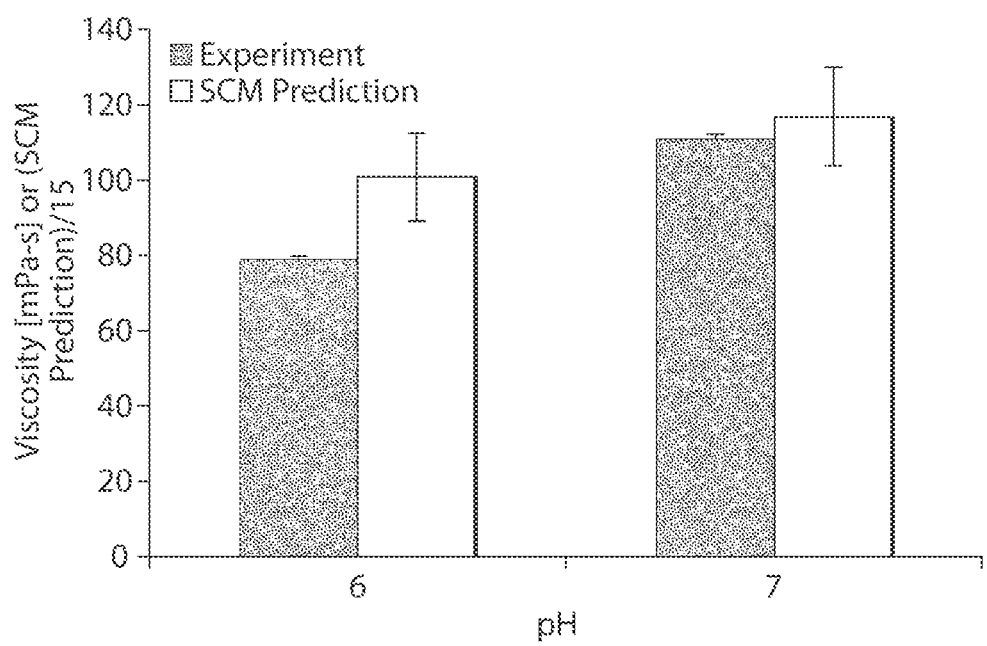
FIG. 3 is a comparison of SCM predictions at two different pH values for mAb6 with experimentally measured viscosity of mAb6. Experiments were performed using 150 mg/ml of mAb6 in 20 mM His buffer. Experimental values are in the first bar of each pair. SCM predicted values are in the second bar of each pair.

Since the SCM-based method uses atomic charges for each atom at the formulation pH, it can be used to predict the dependence of IgG1 viscosity on its formulation pH. In FIGS. 2 and 3, we demonstrate that the SCM-based method is able to correctly predict the increase in viscosity of mAb10 and mAb6 with increasing pH.

Figure 4:
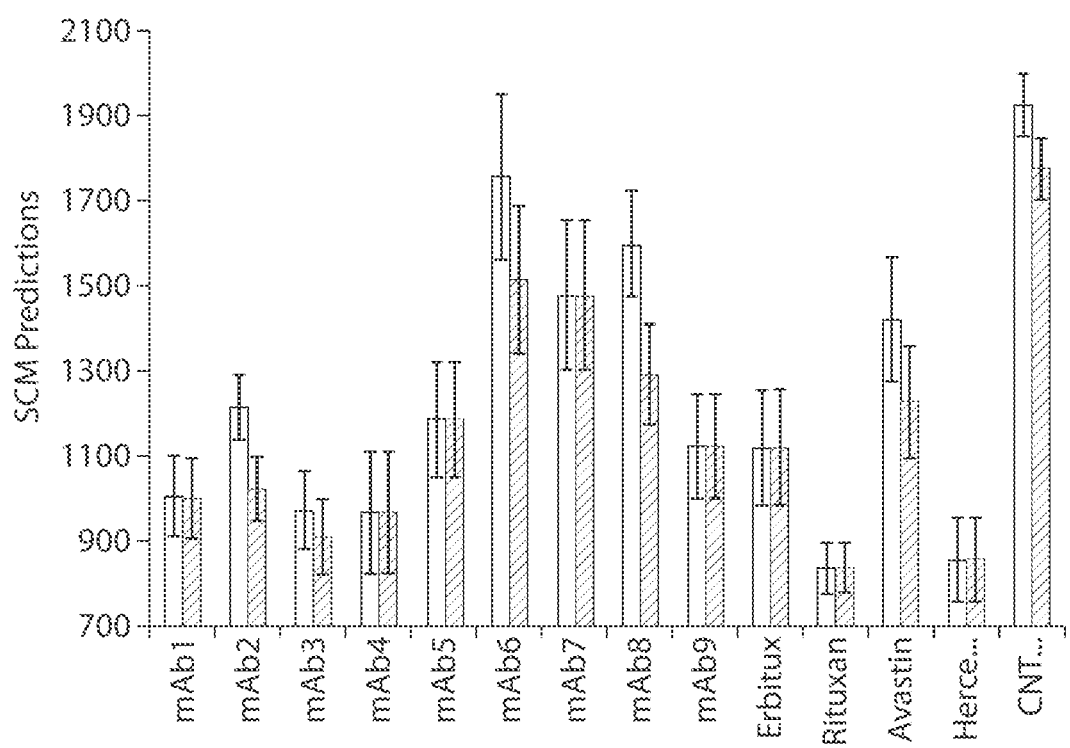
FIG. 4 is a ranking of various IgG1 mAbs for their viscosities at two different pH values using the SCM tool. The first bar for each antibody indicates the SCM prediction at pH ~7 while the second bar indicates SCM prediction at pH ~5.5. The antibodies left to right are mAb1, mAb2, mAb3, mAb4, mAb5, mAb6, mAb7, mAb8, mAb9, Erbitux, Rituxan, Avastin, Herceptin, and CNTO607.

Furthermore, the SCM-based method can be used to perform the viscosity-ranking of antibodies at different formulation pH as shown in FIG. 4. FIG. 4 indicates that while the viscosity of mAb1 and mAb2 will be comparable at pH ~5.5, mAb2 will exhibit slightly higher viscosity than mAb1 at pH ~7. Similarly, the SCM-based method predicts that while at pH ~5.5, mAb6 and mAb7 will exhibit similar viscosities, mAb6 will be more viscous at pH ~7.

The SCM-based method also can be used to engineer antibodies in order to produce antibodies with lower viscosities. The SCM-based method can be used to identify patches of exposed charged residues present on the protein surface. Based on observations on a number of IgG1 antibodies, it was predicted that patches of exposed negative residues on the Fv region (as indicated by the high value of absolute Fv negative SCM Score) are responsible for high viscosity of these IgG1. A similar approach can be taken for other proteins as well.

Figure 5A:
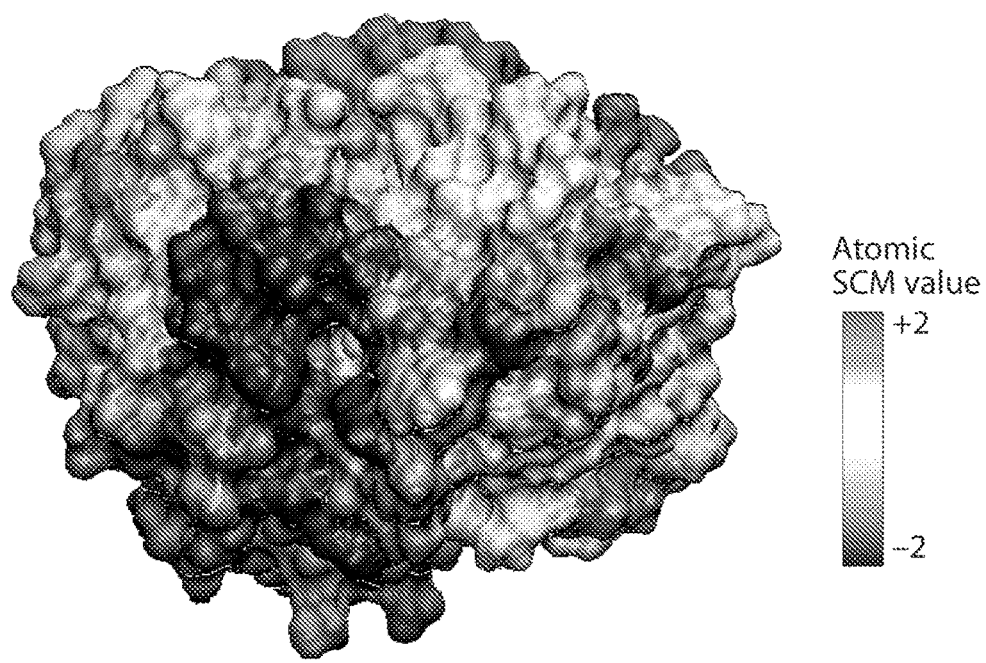
FIGS. 5A and B are illustrations of atomic SCM values projected onto the Fab domain of CNTO607. The regions indicated in red are patches of exposed negative residues and hence antibody variants in which these negative residues are mutated to either neutral or positively-charged residues should display low viscosities.
Figure 5B:
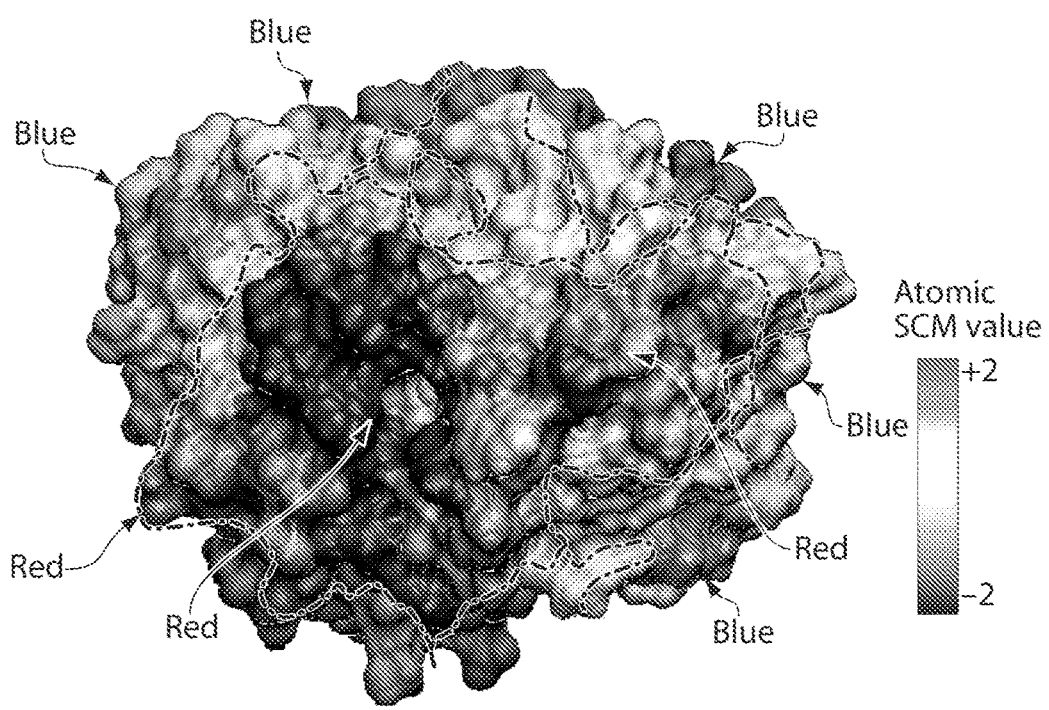
FIG. 5B is a gray scale rendering. The color denotes atomic SCM values with −2 values being in red and +2 values being in blue.

FIG. 5 illustrates atomic SCM values projected onto the Fab domain of CNTO607. The regions indicated in red in FIG. 5 are patches of exposed negative residues and hence antibody variants in which these negative residues are mutated to either neutral or positively-charged residues should display low viscosities.

In some embodiments, an SCM tool, executing on one or more computing devices, may be used to compute a value/score for an antibody that may then be used to predict viscosity of the antibody. "Score," as used herein, refers to a score computed using the SCM tool and is therefore interchangeably referred to as a SCM score. The SCM tool may analyze a representation of one or more tertiary structures of the antibody or a domain of the antibody and compute the SCM score based on a parameter of each atom in the structure, including by analyzing that parameter under a condition. In some embodiments, the parameter may be a partial charge of the atom and the condition may be a pH value, and the SCM tool may compute a score for the antibody at a pH value. The SCM tool may then use the computed SCM score to predict the viscosity of the antibody and identify whether the antibody may be a candidate of interest (e.g., for a candidate suitable for subcutaneous administration).

Figure 6:
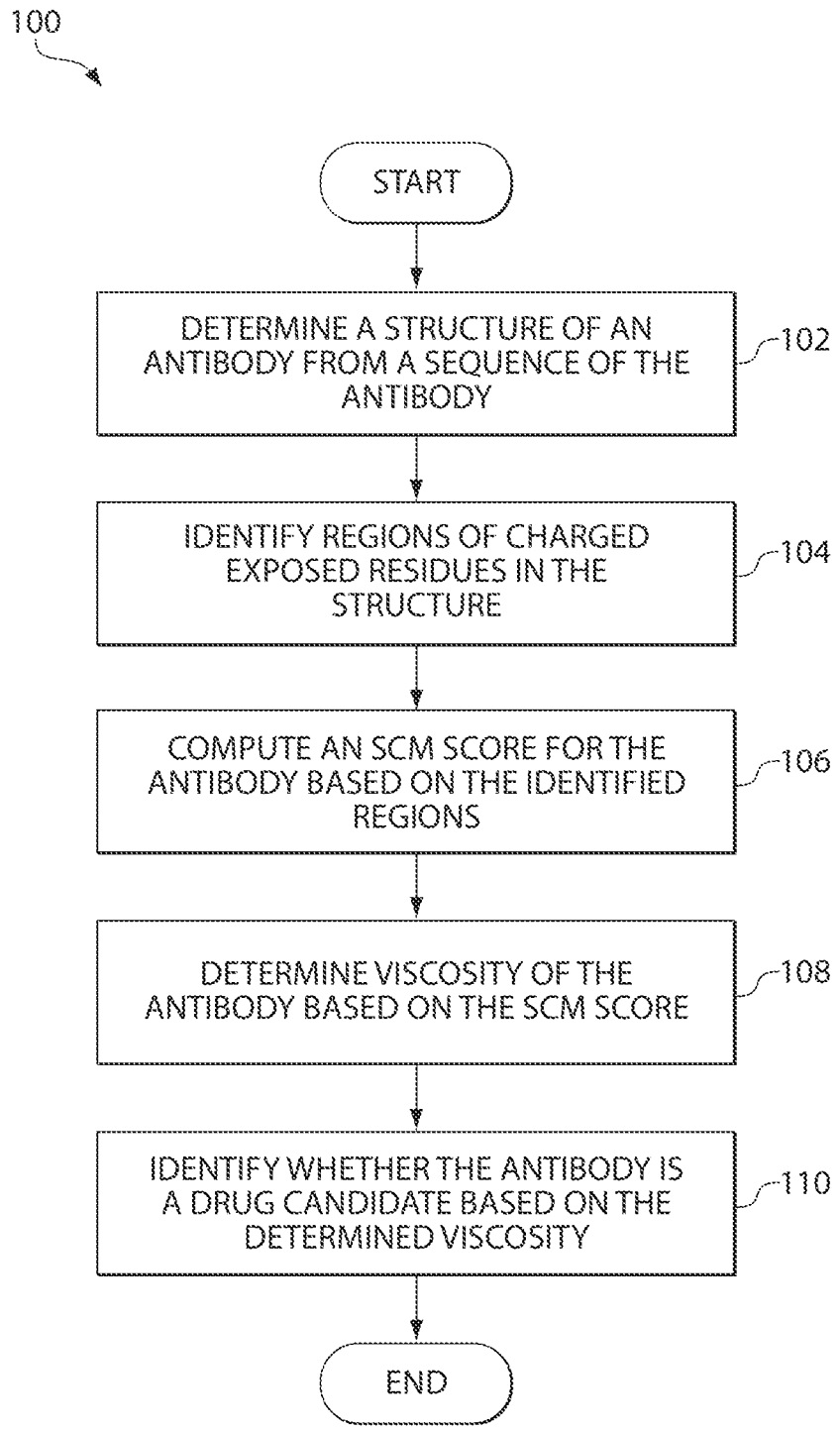
FIG. 6 is a flowchart illustrating generally a process of screening antibodies based on their viscosities, in accordance with some embodiments of the invention. It is to be understood that the invention contemplates generalization of the process to proteins.

FIG. 6 illustrates generally a process 100 of screening antibodies based on their viscosities, in accordance with some embodiments of the invention. At block 102, the SCM tool receives as input a structure of an antibody, which may have been experimentally determined or may have been predicted (e.g., using homology modeling or other techniques) from a sequence of the antibody. The SCM tool may receive the input in any suitable manner, including by receiving the input from another process executing on a same computing device as the SCM tool or by reading the input from one or more storage media. Next, at block 104, the SCM tool analyzes that structure to identify regions of charged exposed residues in the structure. The SCM tool may compute a score for the antibody based on the identified regions, at block 106 and predict a viscosity of the antibody based on the computed SCM score, as shown at block 108. For example, an increase in an absolute value of the SCM score may be correlated with an increase with the viscosity of the antibody. At block 110, the SCM tool may identify, based on the viscosity, whether the antibody may be selected as a candidate for further development. For example, in some embodiments, if the viscosity of the antibody is determined to be low, the antibody or a fragment of the antibody may be selected as a candidate suitable for subcutaneous delivery.

Figure 7:
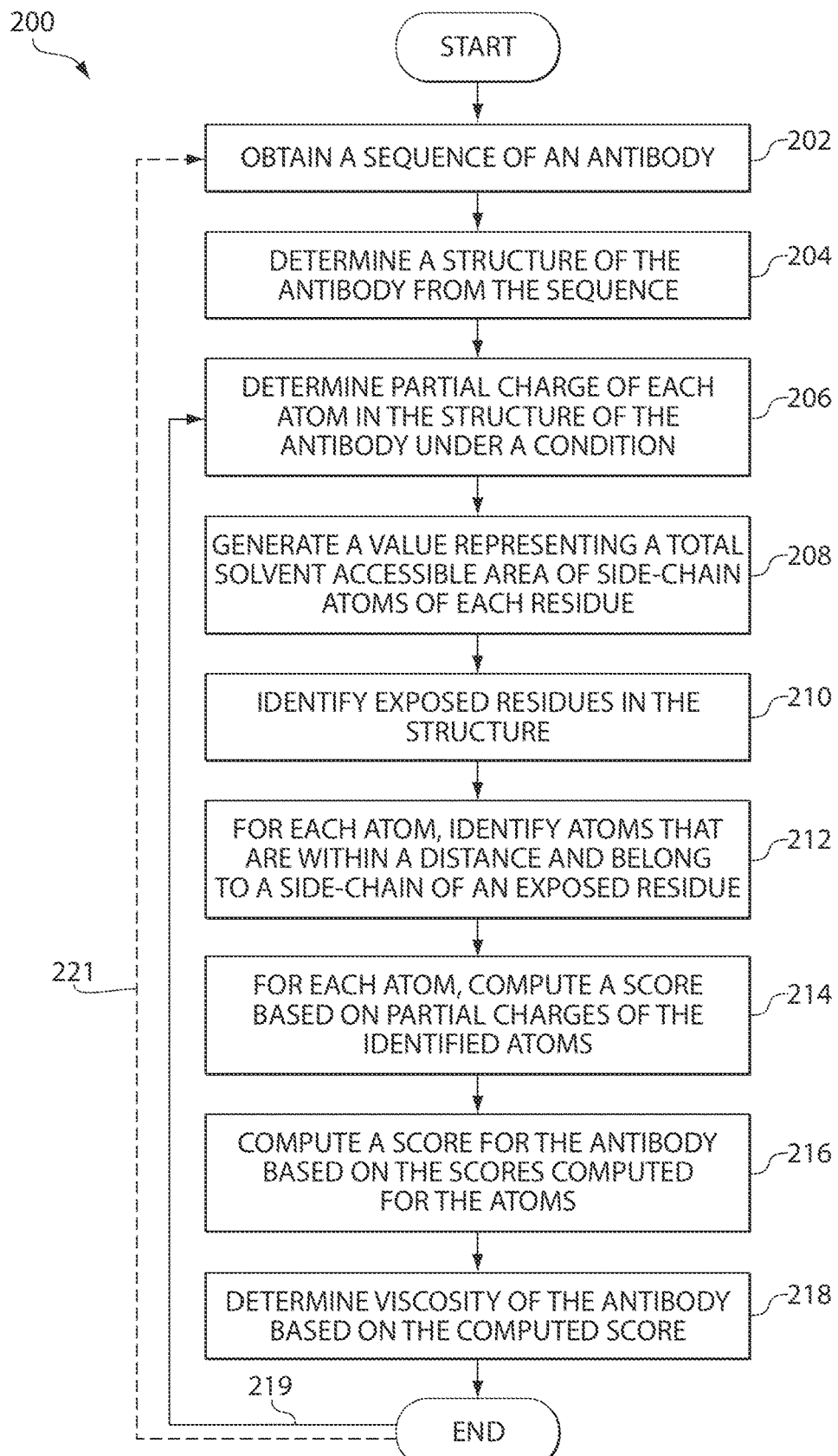
FIG. 7 is a flowchart illustrating a process of determining viscosity of an antibody using a structure of the antibody, in accordance with some embodiments of the invention. It is to be understood that the invention contemplates generalization of the process to proteins. Such a process may be represented or referred to as an algorithm.

FIG. 7 illustrates a process 200 of determining viscosity of an antibody using the SCM tool in accordance with some embodiments of the invention. The tool, according to embodiments of the invention, may be implemented in any suitable way. In some embodiments, the tool may be implemented in a computer system including computer-executable instructions that are executed to compute SCM scores using antibody structures. In some embodiments, the tool may be implemented to be interactive.

The process 200 may start with the SCM tool obtaining, at block 202, a sequence of the antibody. The sequence may be a nucleotide sequence encoding the antibody or an amino acid sequence. The sequence of the antibody may be previously generated sequence which may be obtained from a suitable database. Further, in some embodiments, the antibody may be extracted from a biological sample and sequenced using any suitable techniques. The SCM tool may receive the sequence in any suitable manner, including by receiving the sequence from another process executing on a same computing device as the SCM tool or by reading the sequence from one or more storage media.

Regardless of the way in which the antibody sequence is obtained by the SCM tool, next, at block 204, the SCM tool may determine a structure of the antibody. Alternatively, in block 204 the SCM tool may determine a structure of one or more of portions of the antibody. "Portion," as used herein, refers to a fragment or a domain of the antibody. For the purpose of brevity, the following description refers to the structure of the antibody. However, it should be appreciated that a structure of one or more fragments or domains of the antibody may be analyzed using process 200 as described below.

The structure of the antibody may be a three-dimensional or tertiary structure determined using X-ray crystallography, nuclear magnetic resonance (NMR) spectroscopy, or using any other techniques, as embodiments of the invention are not limited in this respect.

In some embodiments, the structure of the antibody may be determined from the sequence using homology modeling. Any suitable homology modeling technique may be utilized to obtain a model of the structure of the antibody using its sequence. For example, software tools such as WAM, PEGS, Rosetta, Accelrys, MOE, Schrodinger, etc. may be used to predict a structure of an antibody and generate a three-dimensional model of the antibody.

In embodiments in which these techniques (e.g., crystallography, spectroscopy, homology modeling) or others are used, the SCM tool may communicate the sequence obtained in block 202 to one or more hardware and/or software tools that perform these techniques. The tools may be a part of the same computing device(s) as the one(s) on which the SCM tool is executing. For example, the tools may be a peripheral device connected to the same computing device(s) on which the SCM tool is executing, or may be software executing on those same computing device(s). In such embodiments, the SCM tool may use any suitable inter- or intracomputer communication techniques to provide the tool(s) with the sequence obtained in block 202 and to receive information regarding the structure(s) resulting from the analysis performed by the tools. Any suitable information regarding the structure(s), in any suitable format, that is indicative of the structural properties discussed below may be received by the SCM tool, as embodiments are not limited in this respect.

It should be appreciated that, while the process 200 of FIG. 2 includes the SCM tool receiving the sequence and determining the structure in blocks 202-204, in some embodiments the SCM tool may instead receive information regarding the structure of a protein as input.

In some embodiments, more than one structure of the antibody may be determined and analyzed, as described in more detail in connection with FIG. 8.

Because partial charges of a protein molecule depend on a solution pH, the described techniques may be applied to each of the structures at a pH value. Thus, next, at block 206 in FIG. 6, the SCM tool may determine a partial charge of each atom in the structure of the antibody or its domain at a certain condition, such as a pH value. For example, the SCM tool may determine a SCM score for an antibody at pH of greater than or equal to 7, a pH less than or equal to about 5.5, or any other pH value. In some embodiments, partial charge of each atom in the structure of the antibody or its domain may be determined at more than one pH value, with one SCM score being output for each pH.

Any suitable techniques may be used to determine a partial charge of each atom in the structure of the antibody. For example, software tools such as PropKa, Accelrys, Schrodinger, etc. may be used to determine the partial charge on each atom in the structure of the antibody at a pH value. In some embodiments, the partial charges are assigned to the atoms using CHARMM27 force field.

At block 208, for each residue in the antibody, the SCM tool may compute a value representing a solvent accessible area (SAA) of side-chain atoms of the residue. The tool may compute the SAA using any suitable techniques. For example, in some embodiments, the SAA may be computed by analysis of the structure of the antibody using known techniques, with a "probe radius" of 1.4 Å, which approximates the radius of a water molecule. It should be appreciated, however, that any other suitable techniques may be utilized to determine an SAA.

At block 210, the SCM tool may identify exposed residues in the structure based on the computed values of the SAA of the residues. The residues may be defined as exposed based on a threshold, which may be determined in any suitable manner. For example, in some embodiments, all residues with SAA>10 Å$^2$ may be identified as exposed residues. In such instances, residues with SAA<10 Å$^2$ may be identified as buried residues. Though, it should be appreciated that any other thresholds may be used including those in the range of 1-50 Å$^2$, as embodiments of the invention are not limited in this respect.

At block 212, for each atom in the structure of the antibody, the SCM tool may identify a plurality of other atoms that are within a distance R from that atom and belong to a side chain of a residue identified to be exposed at block 210. A score for the atom, such as an SCM score, may then be computed by the SCM tool based on the sum of partial charges of all the other atoms. The SCM tool may compute the SCM score at any value of R which is greater than zero. In some embodiments, R=10 Å may be utilized, though this number is provided by way of example only. In other embodiments, R=5 Å may be used. R values ranging from 5-20 Å can be used, wherein the lower R values provide higher resolution but more noise and the higher R values provide lower resolution but less noise. Though, it should be appreciated that embodiments of the invention are not limited to any particular value of the distance R, and other R values may be substituted.

Further, at block 214, the SCM tool may compute an SCM score for each atom based on partial charges of each of the atoms identified at block 212. The SCM tool may compute the SCM score according the Equation (1), in which a residue is taken as an exposed residue if the total SAA of all the side-chain atoms of this residue in the antibody structure is greater than 10 Å$^2$. As stated herein, the cut-off may range from 1-50 Å$^2$.

After the SCM tool computes SCM scores for all atoms in the structure, the SCM tool may compute a SCM score for the antibody or any domain of the antibody by combining the SCM scores for the atoms. For example, the scores may be computed for the Fab and Fv domains of the antibody using the Equations (2)-(7) shown above.

Next, at block 218, the SCM tool may predict the viscosity of the antibody based on the SCM score computed at block 216. Thus, the SCM score computed for the antibody may be correlated with the viscosity of the antibody. For this purpose, a cutoff or threshold may be used to determine whether the viscosity of the antibody is high or low. For example, an absolute value of the score computed for the antibody may be correlated with the viscosity of the antibody. If the absolute value of the score is above the threshold, the viscosity of the antibody may be determined to be high. Conversely, if the absolute value of the score is less than the threshold, the viscosity of the antibody may be determined to be low. In some embodiments, more than one threshold or cutoff for the score may be utilized and different levels of viscosities of the antibodies may be determined.

Additionally or alternatively, in some embodiments, the viscosity of the antibody may be predicted based on the SCM score by comparing the SCM score to SCM scores of a variety of other antibodies. In such embodiments, viscosity of an antibody may therefore be considered relative viscosity.

After the SCM tool predicts the viscosity of the antibody as shown at block 218 in FIG. 7, process 200 may end. The predicted viscosity may be used in a number of ways. For example, in some embodiments, the predicted viscosity of the antibody may be used to determine whether the antibody may be selected as a candidate for use or further development. For example, if the viscosity of the antibody is determined to be low, the antibody may be selected as a candidate suitable for formulation for parenteral (e.g., subcutaneous) administration. The predicted viscosity may also be used to engineer antibodies to generate antibodies with low viscosities, and for any other suitable purpose.

As discussed above, different SCM scores may be computed at different conditions, such as different pH values. Thus, if another score is desired to be computed for the antibody at a different condition, such as a different pH value, process 200 may return (as shown by an arrow 219 in FIG. 7) to block 206 for the SCM tool to determine partial charge of each atom in the analyzed structure at another pH value. It should be appreciated that the order of processing at blocks 206-218 is shown in FIG. 7 by way of example only. The processing may be performed at any other suitable order. For example, the SCM tool may determine the partial charge of each atom in the analyzed structure, at block 206, at more than one condition. In such scenarios, process 200 may follow to analyze the structures at the conditions at blocks 208-218 simultaneously, so that more than one score is computed for the antibody at block 216, one for each condition. In some embodiments, the SCM tool may compute two SCM scores, each for a different pH value (e.g., at pH of greater than or equal to 7 and at a pH less than or equal to about 5.5), to predict viscosity of an antibody. Though, it should be appreciated that viscosity of an antibody may be predicted using any number of SCM scores computed for an antibody or its fragment using the described techniques, as embodiments of the invention are not limited in this respect.

It should be appreciated that process 200 may execute continuously, and multiple antibodies may be screened based on their viscosities. Thus, as schematically shown by arrow 221 in FIG. 7, process 200 may return to block 202 where the SCM tool may obtain and analyze a sequence of another antibody. In this way, the SCM tool may screen a large number of antibodies as potential candidates. The candidates identified using the described techniques may then be further analyzed.

In some embodiments, more than one structure, or conformation, of an antibody may be determined, and the SCM tool may compute an SCM score for each of the structures. The multiple structures may be predicted, for example, using molecular dynamic simulation techniques. Any number of the structures may be determined for an antibody, including 2, 3, 4, 5, 6, 7, 8, 9, 10, 10-20, 20-30, 30-40, 40-50, 50-60, 60-70, 70-80, 80-90, 90-100 or more.

In such embodiments, the SCM tool may compute an SCM score for an antibody based on the scores computed for each of the multiple structures. For example, the SCM tool may compute a score for the antibody as an average of the scores computed for the multiple structures. It should be appreciated, however, that the scores computed for the multiple structures may be combined in any suitable way to compute the SCM score for the antibody. Any other suitable parameters (e.g., a standard deviation of the scores for the multiple structures) may be computed for the antibody.

Figure 8:
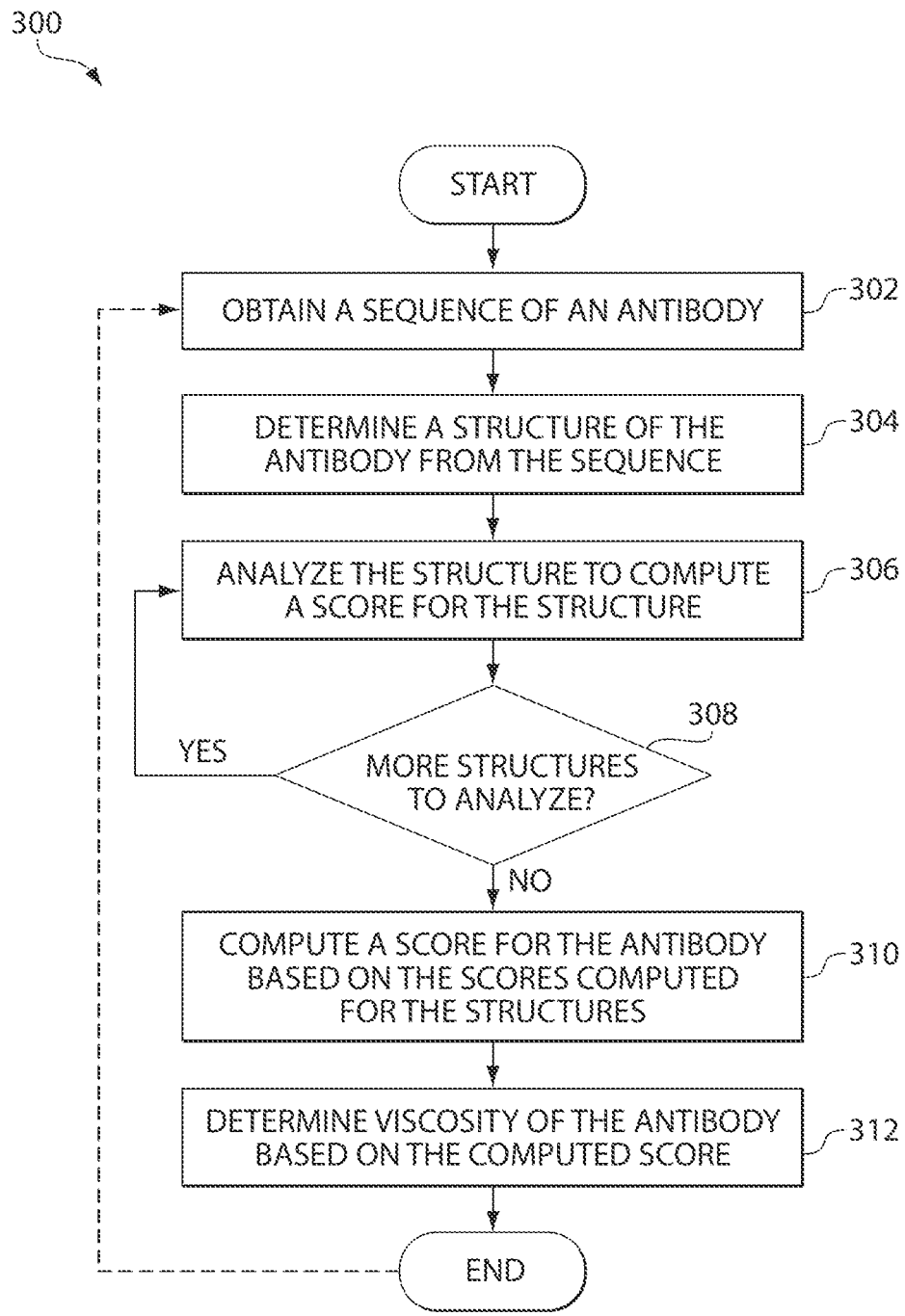
FIG. 8 is a flowchart illustrating a process of determining viscosity of an antibody using multiple structures of the antibody, in accordance with some embodiments of the invention. It is to be understood that the invention contemplates generalization of the process to proteins. Such a process may be represented or referred to as an algorithm.

FIG. 8 illustrates a process 300 that an SCM tool may implement for determining viscosity of an antibody using multiple structures of the antibody, in accordance with some embodiments of the invention. Processing at block 202 in FIG. 8 may be similar to obtaining a sequence of the antibody at block 202 in FIG. 7. At block 304 in FIG. 8, the SCM tool may determine a structure of the antibody (e.g., generated experimentally or predicted using suitable techniques), similarly to processing at block 204 in FIG. 7. The SCM tool may then at block 306 analyze a structure of the antibody determined at block 304 to compute a score, such as an SCM score, for the structure. The processing at block 306 in FIG. 8 may be similar to processing at blocks 206-216 in FIG. 7, and is therefore not described herein in detail.

After the SCM tool computes the SCM score for the structure of the antibody, the tool may determine, at decision block 308, whether there are more structures of the antibody to be analyzed. If the tool determines, at block 308, that there are more structures of the antibody to be analyzed, process 300 may return to block 304 where another structure of the antibody may be generated and analyzed by the tool at block 306. In this way, the SCM tool may generate multiple SCM scores for an antibody.

If it is determined, at block 308, that there are no further structures of the antibody to be analyzed, process 300 may follow to block 310, where the SCM tool may compute an SCM score for the antibody based on multiple scores computed for different structures. The tool may then predict a viscosity of the antibody based on the computed SCM score, at block 312.

In some embodiments, the SCM tool may present the computed SCM scores on a display in a suitable manner. For example, the SCM tool may map atomic SCM values on a representation of a surface of the antibody, and may color each atom of the protein according to its SCM value. For example, the SCM tool may represent an atom with a SCM value>0 using one color, and represent an atom with a SCM value<0 using a different color. Furthermore, the SCM tool may present the scores using various types of charts, plots, tables, diagrams and any other visual representation formats. Though, it should be appreciated that the scores computed using the SCM tool may be presented in any suitable manner.

Figure 9:
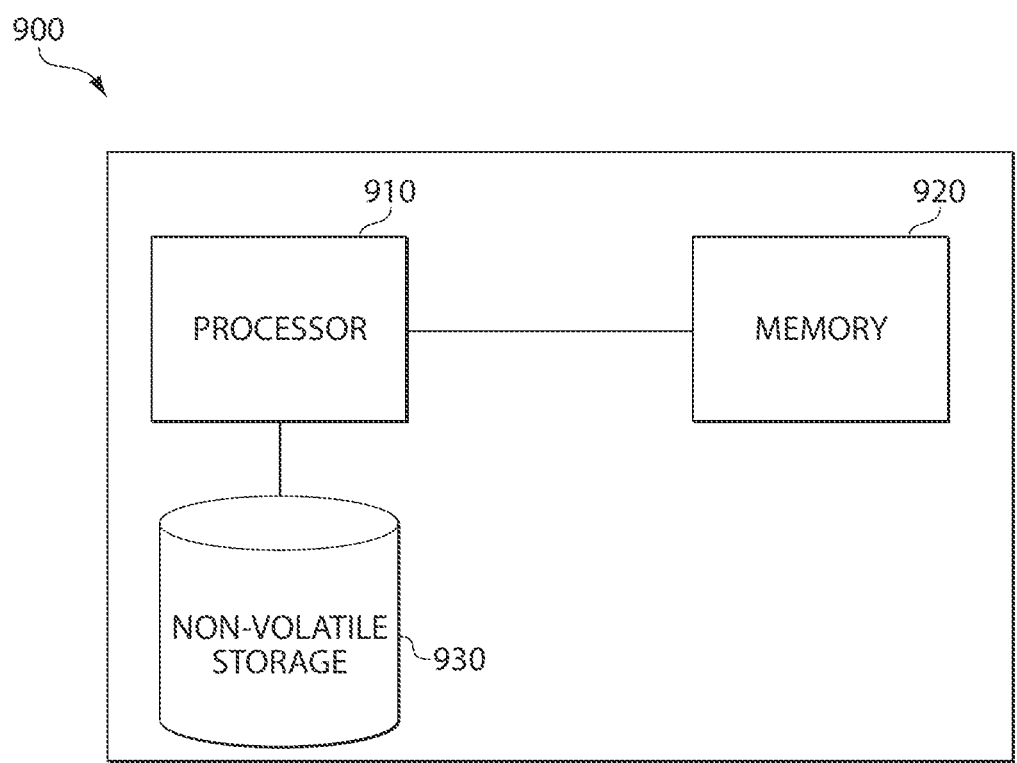
FIG. 9 is a block diagram of an exemplary computing environment on which some embodiments of the invention may be implemented.

In some embodiments, at least some processing steps performed by the SCM tool may be implemented as computer-readable instructions stored on one or more non-transitory computer-readable storage media which, when executed by one or more processors, cause a computing device to execute the steps. An exemplary implementation of a computer system 900 in which some embodiments of the invention may be implemented is shown in FIG. 9. The computer system 900 may include one or more processors 910 and one or more computer-readable non-transitory storage media (e.g., memory 920 and one or more non-volatile storage media 930). The processor 910 may control writing data to and reading data from the memory 920 and the non-volatile storage device 930 in any suitable manner, as the aspects of the present invention described herein are not limited in this respect. To perform any of the functionality described herein, the processor 910 may execute one or more computer-executable instructions stored in one or more computer-readable storage media (e.g., the memory 920), which may serve as non-transitory computer-readable storage media storing instructions for execution by the processor 910. It should be appreciated that the computer system 900 may include any other suitable components.

The above-described embodiments of the present invention may be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present invention comprises at least one non-transitory computer-readable storage medium (e.g., a computer memory, a floppy disk, a compact disk, a tape, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Proteins

The methods of the invention may be used to screen proteins. Proteins that may be screened are typically those intended for use in vivo as for example a therapeutic or a diagnostic. Such proteins may be used as whole proteins or as fragments thereof including domains thereof. Examples of proteins include but are not limited to antibodies (described in greater detail below), hormones, cytokines such as interleukins, growth factors (including those that may be used to stimulate growth of cells in vivo including for example G-CSF), enzymes (including those that may be used in enzyme replacement therapy), and the like.

Antibodies

As used herein, the term "antibody" refers to a whole antibody. An antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three subdomains, $C_{H1}$, $C_{H2}$ and $C_{H3}$. Each light chain is comprised of a light chain variable region (abbreviated herein as $V_L$) and a light chain constant region. The light chain constant region is comprised of one subdomain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies fragments may be described in terms of proteolytic fragments including without limitation Fv, Fab, Fab' and F(ab')$_2$ fragments. Such fragments may be prepared by standard methods (see, e.g., Coligan et al. *Current Protocols in Immunology*, John Wiley & Sons, 1991-1997, incorporated herein by reference). An antibody may comprise at least three proteolytic fragments (i.e., fragments produced by cleavage with papain): two Fab fragments, each containing a light chain domain and a heavy chain domain (designated herein as a "Fab heavy chain domain") and one Fc fragment containing two Fc domains. Each light chain domain contains a $V_L$ and a $C_L$ subdomain, each Fab heavy chain domain contains a $V_H$ and a $C_{H1}$ subdomain, and each Fc domain contains a $C_{H2}$ and $C_{H3}$ subdomain.

As used herein, the term "monoclonal antibody" refers to an antibody obtained from a single clonal population of immunoglobulins that bind to the same epitope of an antigen. Monoclonal antibodies have the same Ig gene rearrangement and thus demonstrate identical binding specificity. Methods for preparing monoclonal antibodies are known in the art.

As used herein, "humanized monoclonal antibody" may refer to monoclonal antibodies having at least human constant regions and an antigen-binding region, such as one, two or three CDRs, from a non-human species. Humanized antibodies specifically recognize antigens of interest, but will not evoke an immune response in humans against the antibody itself.

As used herein, the term "chimeric antibody" refers to a monoclonal antibody comprising a variable region from one source (e.g., species) and at least a portion of a constant region derived from a different source. In some embodiments, the chimeric antibodies comprise a murine variable region and a human constant region.

REFERENCES

1. Yadav, S., Shire, S. J. & Kalonia, D. S. Viscosity Behavior of High-Concentration Monoclonal Antibody Solutions: Correlation with Interaction Parameter and Electroviscous Effects. Journal of pharmaceutical sciences 101, 998-1011 (2012).
2. Yadav, S., Shire, S. J. & Kalonia, D. S. Viscosity analysis of high concentration bovine serum albumin aqueous solutions. Pharmaceutical research 28, 1973-83 (2011).
3. Yadav, S., Laue, T. M., Kalonia, D. S., Singh, S. N. & Shire, S. J. The influence of charge distribution on self-association and viscosity behavior of monoclonal antibody solutions. Molecular pharmaceutics 9, 791-802 (2012).
4. Bethea, D. et al. Mechanisms of self-association of a human monoclonal antibody CNTO607. Protein engineering, design & selection: PEDS 25, 531-7 (2012).
5. Teplyakov, A. et al. Epitope mapping of anti-interleukin-13 neutralizing antibody CNTO607. Journal of molecular biology 389, 115-23 (2009).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

Having described several embodiments of the invention in detail, various modifications and improvements will readily occur to those skilled in the art. Such modifications and improvements are intended to be within the spirit and scope of the invention.

What is claimed is:

1. A method for producing a low-viscosity antibody solution, the method comprising:
    (a) identifying surface-exposed amino acid residues in tertiary structures of a plurality of antibodies by computing total solvent accessible area (SAA) values for amino acid residues of the antibodies based on partial charge values assigned to side-chain atoms of the antibodies, wherein an amino acid residue is identified as a surface-exposed amino acid residue if it has a SAA of greater than a threshold value;
    (b) identifying atoms that are within a distance R and belong to a side-chain of an exposed amino acid residues identified in (a);
    (c) computing an atomic spatial charge map (SCM) value for each atom identified in (b), wherein the atomic SCM value is the sum of partial charges of the atoms identified in (b);
    (d) computing a SCM score for each of the antibodies based on the atomic SCM values computed in (c); and
    (e) predicting relative viscosity of each of the antibodies based on the SCM score computed in (d) by comparing the SCM scores computed in (d) to each other, wherein an antibody is predicted to have a low viscosity if the SCM score computed in (d) is lower than the SCM scores of the other antibodies of the plurality; and
    (f) producing a solution comprising the antibody predicted to have a low viscosity.

2. The method of claim 1, wherein the tertiary structure of the antibodies is a Fab domain or a Fv domain of the antibody.

3. The method of claim 1, wherein the partial charge in step (a) is assigned using a software tool selected from CHARMM force field, PropKa, Accelrys, and Schrodinger.

4. The method of claim 1, wherein the threshold value is 1-50 $Å^2$.

5. The method of claim 1, wherein the distance R is 5-20 Å.

6. The method of claim 4, wherein the threshold value is 10 $Å^2$.

7. The method of claim 5, wherein the distance R is 10 Å.

8. The method of claim 1, wherein the atomic SCM value in (c) is computed based on a pH value of greater than or equal to 7.

9. The method of claim 1, wherein the atomic SCM value in (c) is computed based on a pH value of less than or equal to 5.5.

10. The method of claim 1, wherein the antibody is a monoclonal antibody.

11. The method of claim 1, wherein the antibody is an antibody fragment.

12. The method of claim 11, wherein the antibody fragment is a Fv, Fab, Fab' or F(ab')2 fragment.

* * * * *